United States Patent [19]

Heller et al.

[11] Patent Number: 5,461,140

[45] Date of Patent: * Oct. 24, 1995

[54] BIOERODIBLE POLYMERS FOR SOLID CONTROLLED RELEASE PHARMACEUTICAL COMPOSITIONS

[75] Inventors: Jorge Heller, Woodside; Steve Y. W. Ng, San Francisco, both of Calif.

[73] Assignee: Pharmaceutical Delivery Systems, Menlo Park, Calif.

[*] Notice: The portion of the term of this patent subsequent to Jul. 9, 2008 has been disclaimed.

[21] Appl. No.: 153,537

[22] Filed: Nov. 15, 1993

Related U.S. Application Data

[63] Continuation of Ser. No. 877,947, Apr. 30, 1992, abandoned.

[51] Int. Cl.$^6$ .................................................. C08G 65/34
[52] U.S. Cl. ........................ 528/425; 424/486; 424/423; 424/457; 514/179; 568/831
[58] Field of Search .................................. 424/486, 423, 424/457; 514/179; 528/425; 568/831

[56] References Cited

U.S. PATENT DOCUMENTS

| | | | |
|---|---|---|---|
| 3,057,815 | 8/1962 | Bartlett et al. | 524/285 |
| 3,306,875 | 2/1967 | Hay | 521/25 |
| 4,066,747 | 1/1978 | Capozza | 424/78 |
| 4,079,038 | 3/1978 | Choi et al. | 528/196 |
| 4,119,579 | 10/1978 | Capozza | 526/270 |
| 4,122,158 | 10/1978 | Schmitt | 424/27 |
| 4,186,185 | 1/1980 | Capozza | 424/19 |
| 4,304,767 | 12/1981 | Heller et al. | 424/78 |
| 4,405,798 | 9/1983 | Hall et al. | 549/363 |
| 4,549,010 | 10/1985 | Sparer et al. | 528/361 |
| 4,814,173 | 3/1989 | Song et al. | 424/444 |
| 5,030,457 | 7/1991 | Ng et al. | |
| 5,336,505 | 8/1994 | Ng et al. | 424/486 |

FOREIGN PATENT DOCUMENTS

0208617A1  1/1987  European Pat. Off. .

OTHER PUBLICATIONS

Burt et al.; *J. Am. Chem. Soc* (1982); 104:3687–3690.
Heller et al.; *Biomaterials* (1990); 11:235–237.
Heller et al.; *Macromolecules* (1992); 25(13):3362–3364.
Padias et al.; *Macromolecules* (1982); 15(2):217–223.
Padias et al.; "Synthesis and Polymerization of Atom–Bridged Bicyclic Acetyls and Ortho Esters; a New Mechanism"; pp. 258–259.
Padias et al.; "Synthesis and Polymerization of Atom–Bridged Bicyclic Acetyls and Ortho Esters"; ACS Symposium Series, American Chemical Society, Washington, D.C. (1985); 286:313–333.
Pulapura et al.; *Biomaterials* (1990); 11:666–678.
Szymanski et al.; *J. Polymer Sci.* (1983); 21:177–187.
Yokoyama et al.; *Adv. Polymer Sci.* (1982); 42:109–138.
J. Schmorak, "The Chemistry of Cellulose and Wood" Acad. of Science. USSR. pp. 62–71. (1966).

*Primary Examiner*—James J. Seidleck
*Assistant Examiner*—Terressa Mosley
*Attorney, Agent, or Firm*—Burns, Doane, Swecker & Mathis

[57] ABSTRACT

Bioerodible ortho ester polymers useful for preparing solid form bioerodible pharmaceutical compositions such as pellets, capsules, suppositories and the like are provided. A novel synthetic method for preparing the polymers is provided as well as is a novel triol reactant. Synthesis involves a one-step reaction between a monomeric ortho ester and a triol. The pharmaceutical compositions of the invention are useful for the controlled release of therapeutic agents, and may be administered for a variety of purposes.

28 Claims, No Drawings

BIOERODIBLE POLYMERS FOR SOLID CONTROLLED RELEASE PHARMACEUTICAL COMPOSITIONS

This application is a continuation of U.S. application Ser. No. 07/877,847 filed on Apr. 30, 1992 now abandoned.

TECHNICAL FIELD

The present invention is in the field of polymer chemistry and drug delivery. It concerns certain ortho ester polymers and methods for their preparation. These materials are bioerodible polymers, i.e., polymers containing hydrolytically labile linkages which undergo cleavage at physiologic conditions. These bioerodible polymers are useful for the controlled release of therapeutic agents. More specifically, the invention relates to solid drug dosage forms such as bioerodible pellets, capsules, suppositories and the like formulated with bioerodible polymers, and to the use of these solid bioerodible dosage forms in the treatment of disease conditions.

BACKGROUND OF THE INVENTION

Bioerodible polymers used to control the release of therapeutic agents physically dispersed in the polymer matrix have been described in a variety of contexts. One matrix which has been successful is a family of poly(ortho esters). These materials contain the pH-sensitive ortho ester linkage in their polymer backbone. Such polymers are described, for example, in U.S. Pat. No. 4,304,767 to Heller et al. Because the ortho ester linkages within these polymers are relatively stable at neutral pH, and hydrolyze progressively faster with the decreasing pH of the surrounding medium, the rate of erosion of the polymer can be manipulated within a very wide range by incorporating various levels and strengths of acidic excipients into the polymer matrix.

The method of preparing polymers according to the aforementioned patent comprises the addition of polyols to diketene acetals as shown in Scheme 1.

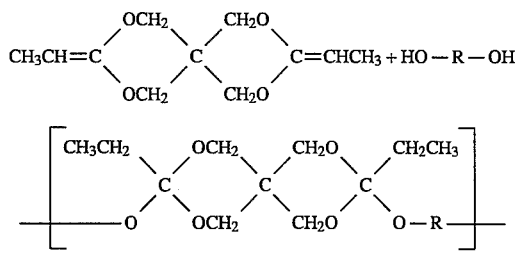

Using this scheme, almost any diketene acetal and any diol can be used, and the synthetic method is thus extremely versatile. Polymers synthesized by this method are, however, not optimal for preparing soft or amorphous drug dosage forms such as bioerodible ointments, creams or gels due to the relatively rigid pentaerythritol segment in the polymer backbone.

Polymers and the method of preparing polymers for use in soft drug dosage forms are described in U.S. Pat. No. 5,030,457 to Ng et al. The method described in this patent involves reacting a monomeric ortho ester with a triol to form a polymer.

The polymers synthesized as described in U.S. Pat. No. 5,030,457 have the desirable properties of being able to undergo bioerosion and of being less rigid and more flexible and conforming than prior ortho ester polymers. Polymers synthesized by this method are, however, not optimal for preparing solid drug dosage forms.

There is thus a need in the art for a bioerodible composition which has a molecular structure of sufficient rigidity to enable its use as a bioerodible matrix in solid dosage forms such as pellets, capsules, suppositories or the like. An ideal material would enable the local or systemic delivery of an effective dose level of pharmaceutical agent from a subcutaneous pellet or the like at a desired rate for a period of time dictated only by clinical considerations and not by limitations of the solid dosage formulation. The ability to achieve this is particularly important with agents which when administered in an uncontrolled manner can produce serious side effects. The present invention provides bioerodible pellets, capsules, suppositories, etc., from which the release rate of the drug to be delivered—as well as the desired time period for drug delivery—can be carefully controlled. It provides materials which bioerode to small, water-soluble molecules that leave no residues in the tissue of the patient undergoing treatment. The invention thus enables improved treatment of a variety of disease states by the controlled delivery of drugs over prolonged periods of time.

SUMMARY OF THE INVENTION

It is accordingly a primary object of the present invention to address the aforementioned needs in the art, and to provide bioerodible compositions in solid dosage form for the controlled release of therapeutic agents.

It is another object of the invention to provide such bioerodible compositions in the form of bioerodible pellets, capsules, suppositories or the like.

It is still another object of the invention to provide a novel method of synthesizing certain bioerodible ortho ester polymers useful for such compositions.

It is yet a further object of the invention to provide certain novel bioerodible ortho ester polymers having the structure

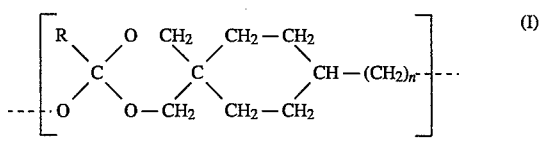

wherein R is hydrogen or alkyl and n is an integer in the range of 1 to 5 inclusive.

It is a further object of the invention to provide a novel triol of the following structure:

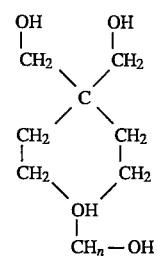

wherein n is as above.

It is still a further object of the invention to provide ortho ester copolymers prepared by reacting a mixture of such triols with a monomeric ortho ester as will be described below.

Additional objects, advantages and novel features of the invention will be set forth in part in the description which follows, and in part will become apparent to those skilled in the art upon examination of the following, or may be learned by practice of the invention.

These objects are achieved by the present invention. In accord with this invention, a method is provided for synthesizing a bioerodible ortho ester polymer. This method involves:

reacting a monomeric ortho ester having the general formula $$R-\underset{\underset{OR'}{|}}{\overset{\overset{OR'}{|}}{C}}-OR'$$

wherein R is as defined above and the R' are independently selected from lower alkyls, with a triol as shown above. This reaction forms an ortho ester polymer containing a mer unit having the following general formula (I)

$$\left[\begin{array}{c} \cdots\text{-}O \end{array}\overset{R}{\underset{O-CH_2}{\diagdown C \diagup}}\overset{O-CH_2}{\underset{CH_2-CH_2}{\diagdown C \diagup}}\overset{CH_2-CH_2}{\underset{CH_2-CH_2}{\diagdown CH-(CH_2)_{n^-}}}\right]\cdots \quad (I)$$

wherein R and n are as just described.

DETAILED DESCRIPTION OF THE INVENTION

A. Definitions

Before the present invention is disclosed and described in detail, it is to be understood that this invention is not limited to specific therapeutic agents, dosage forms, or the like, as such components may, of course, vary. It is also to be understood that the terminology used herein is for the purpose of describing particular embodiments only and is not intended as limiting.

It must be noted that, as used in the specification and the appended claims, the singular forms "a", "an" and "the" include plural referents unless the context clearly dictates otherwise. Thus, for example, reference to "a polymer" includes mixtures of polymers, reference to "a therapeutic agent" includes mixtures of therapeutic agents, and the like.

The term "mer" is used to mean the structurally recurring units or monomer units of the ortho ester polymers provided by the present invention. The mer units of any given polymer may be the same or different; when different, they may be arranged in block or random fashion. When all the mer units of a polymer are the same, the polymer is called a homopolymer. When there are 2 or more mer units in a polymer, the polymer is called a copolymer. The present invention involves both homopolymers and copolymers.

The term "bioerodible" as used herein to describe the polymers of the present invention is synonymous with the term of art "biodegradable." These terms denote the property of a body of solid gel polymer to undergo degradation, erosion and solubilization as a result of hydrolysis of labile linkages at the physiologic conditions of use.

The terms "therapeutic agent" or "drug" are used interchangeably to mean a compound or composition of matter which, when administered to an organism (human or animal) induces a desired pharmacologic and/or physiologic effect by local and/or systemic action. In general, the terms include the therapeutic or prophylactic agents in all major therapeutic/prophylactic areas of medicine.

The term "effective amount" as used herein intends that quantity of a therapeutic agent that, when administered to a patient, is required to provide the desired or intended beneficial effect without intolerable side effects, such as toxicity. When used in the context of controlled or prolonged delivery of drug, the term can include a temporal aspect—noting that the rate of administration gives the desired effect without intolerable side effects.

The term "alkyl" is intended to mean linear, branched or cyclic alkyl moieties having 1 to 10 carbon atoms, inclusive. "Lower alkyl intends an alkyl group of 1 to 5, more typically 1 to 3, carbon atoms.

B. Synthetic Method

In the synthesis aspect of the present invention, a method is provided for synthesizing certain bioerodible ortho ester polymers. The synthesis is a simple, straightforward reaction which may be accomplished in one step in a single reaction vessel. The synthesis involves the reaction of a monomeric ortho ester having the general formula $$R-\underset{\underset{OR'}{|}}{\overset{\overset{OR'}{|}}{C}}-OR'$$

wherein R is a hydrogen or an alkyl of 1 to 10 carbon atoms and the R' are independently selected from lower alkyl, with a triol having the general formula $$\begin{array}{c} \overset{OH}{\underset{CH_2}{|}} \quad \overset{OH}{\underset{CH_2}{|}} \\ \diagdown C \diagup \\ \diagup \quad \diagdown \\ CH_2 \quad CH_2 \\ | \quad | \\ CH_2 \quad CH_2 \\ \diagdown \quad \diagup \\ OH \\ | \\ (CH_2)_n-OH \end{array}$$

wherein n is an integer in the range of 1 to 5 inclusive, preferably 1 to 3.

The reaction is carried out to form an ortho ester polymer which comprises mer units of the structure (I)

$$\left[\begin{array}{c} \cdots\text{-}O \end{array}\overset{R}{\underset{O-CH_2}{\diagdown C \diagup}}\overset{O-CH_2}{\underset{CH_2-CH_2}{\diagdown C \diagup}}\overset{CH_2-CH_2}{\underset{CH_2-CH_2}{\diagdown CH-(CH_2)_{n^-}}}\right]\cdots \quad (I)$$

In preferred embodiments, the R moiety of the monomeric ortho ester reactant is a lower alkyl, the R' moieties are the same and are either methyl or ethyl.

The synthesis of the ortho ester polymer from the monomeric other ester and triol is carried out either neat or, preferably, in an aprotic solvent such as tetrahydrofuran (THF), cyclohexane, ethylene glycol dimethyl ether (glyme), diglyme, cymene, cumene, chlorinated hydrocarbons, or the like. Typical concentrations of the two reactants can range from essentially 100% (neat) down through about 10% by weight or lower, when solvent is used. In either case, care must be taken to maintain anhydrous conditions. The reaction can be carried out at reflux and thus, depending upon the solvent, at temperatures in the range of about 50°–150° C., preferably about 50°–90° C. The approximate molar ratio of reactants is set at about 1:1 if it is desired to maximize the molecular weight of the polymer, but can be varied if a lower molecular weight polymer is desired. It is typically preferred to carry out the reaction in the presence of an acid catalyst, although in cases where the reactants are acidic, a catalyst is unnecessary. Examples of suitable acid catalysts include p-toluenesulfonic acid and methanesulfonic acid. The amount of acid catalyst can range from 0% (based on its optional presence) to about 1% molar (based on the amount of triol present).

The two reactants may be readily synthesized using conventional techniques, or they may be obtained commercially, e.g., from the Aldrich Chemical Company, Milwaukee, Wis. Triols wherein n is greater then 1 may be prepared by reacting the salt

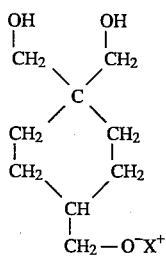

(wherein $X^+$ is a monovalent cation such as $Na^+$) with an alcohol $HO-(CH_2)_{n-1}-Y$ where n is as defined earlier and Y is a leaving group.

Ortho ester copolymer may be prepared by using an admixture of triols rather than a single triol, e.g.., using two or more triols differing with respect to the integer "n".

C. Novel Polymers

The novel ortho ester polymers provided by the present invention contain recurring mer units represented by Formula (I)

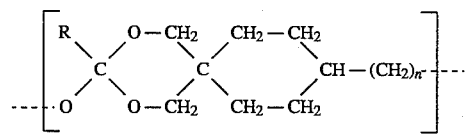

wherein R is hydrogen or an alkyl of 1 to 10 carbon atoms, preferably a linear alkyl, more preferably a linear alkyl of 1 to 6 carbon atoms, and n is 1 to 10, preferably 1 to 5, more preferably 1 to 3.

Typically, although not necessarily, the polymers have molecular weights of at least about 5,000, more preferably at least about 20,000, and most preferably at least about 50,000, and the number of repeating mer units in the polymer will normally be in the range of 2 to 1000, preferably 2 to 200, and most preferably 5 to 200.

These polymers have the desirable properties of being able to undergo bioerosion and of being more rigid and less flexible and conforming than prior ortho ester polymers.

D. Pharmaceutical Compositions

The pharmaceutical compositions of this invention comprise a selected therapeutic agent or number of agents dispersed in a novel bioerodible ortho ester polymer as described in the preceding section. While the preferred pharmaceutical compositions of the invention are injectable bioerodible pellets and similar solid dosage forms adapted for the local or systemic administration of therapeutic agents, other compositional forms (e.g., capsules, suppositories and more rigid transdermal forms) and modes of administration (e.g., transdermal) are within the scope of the invention as well.

The bioerodible dosage forms of the invention will typically include a pellet, capsule or suppository base comprising one or more of the bioerodible ortho ester polymers described herein and a selected therapeutic agent. The therapeutic agent, whether present as a liquid, a finely divided solid, or any other physical form, is dispersed in the pellet, capsule or suppository base. Typically, but optionally, the compositions include one or more other components, e.g., nontoxic auxiliary substances such as colorants, diluents, odorants, carriers, excipients, stabilizers or the like.

The amount of active agent will be dependent upon the particular drug employed and condition being treated. Typically the amount of drug represents about 0.001% to about 70%, more typically about 0.001% to about 50%, most typically about 0.001% to about 20% by weight of the total composition being common.

The quantity and type of ortho ester polymer incorporated into the pellet, capsule, suppository, etc., is variable. For a more rigid, less flexible composition, a higher molecular weight polymer is used. If a less rigid, more flexible composition is desired, a lower molecular weight polymer can be employed, i.e., one which is prepared with other than a 1:1 reactant ratio. The product may be based on only one polymer or it may comprise a mixture of polymers.

While not essential for transdermal administration of many drugs, it may in some cases, with some drugs, be preferred that a skin permeation enhancer be coadministered therewith. Any number of the many skin permeation enhancers known in the art may be used. Examples of suitable enhancers include dimethylsulfoxide (DMSO), dimethylformamide (DMF), N,N-dimethylacetemide (DMA), desylmethylsulfoxide ($C_{10}MSO$), ethanol, eucalyptol, lecithin, and the 1-N-dodecylcyclazacycloheptan-2-ones (available under the trademark Azone® from the Nelson Research and Development Company, Irvine, Calif.).

It is additionally preferred to incorporate an acidic excipient into the bioerodible dosage form in order to control the rate of polymer bioerosion. The ortho ester linkages of the bioerodible polymers are relatively stable at basic or neutral pH and are hydrolyzed at progressively increasing rates as the pH of the medium surrounding the polymer decreases. Thus, hydrolytic lability and the rate of erosion and drug release can be increased by incorporation of one or more acidic components. Preferred acidic excipients are aliphatic acids, typically present at 0–10 wt. %, more preferably 1–5 wt. %, of the bioerodible composition. Solid but water soluble aliphatic acids are generally favored. Examples of acidic excipients useful in conjunction with the present invention include adipic, citric, suberic, maleic and itaconic acids. Basic excipients may also be used to slow the rate of release.

The variety of different therapeutic agents which can be used in conjunction with the bioerodible compositions of the invention is vast. In general, therapeutic agents which may be administered via the pharmaceutical compositions of the invention include, without limitation: antiinfectives such as antibiotics and antiviral agents; analgesics and analgesic combinations; anorexics; antihelminthics; antiarthritics; antiasthmatic agents; anticonvulsants; antidepressants;

antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers.

In preferred embodiments the therapeutic agents for administration in conjunction with the bioerodible polymers of the invention include steroid drugs, antihypertensive agents, anti-allergy medications, and thyroid-related drugs. Examples of steroid drugs useful herein include: progestogens such as norethindrone, norethindrone acetate, desogestrel, 3-keto desogestrel, gestadene and levo norgestrel; estrogens such as estradiol and its esters; corticosteroids such as cortisone, hydrocortisone and fluocinolone acetonide; and testosterone. Antihypertensive agents include, for example, reserpine, pindolol, timolol maleate, bufeniode, indoramin hydrochloride, minoxidil, sodium nitroprusside and captopril. Anti-allergy medications which may be administered using the dosage forms of the invention include chlorphenamine, dexamethasone, epinephrine and prednisolone. Thyroid medications include, for example, levothyroxine sodium, acetiromate, iodothyroglobulin, propylthiouracil, and the like. Other specific compounds within the aforementioned classes will be known to those skilled in the art or may be found, for example, in Korolkovas, *Essentials of Medicinal Chemistry*, 2nd Ed. (New York: Wiley-Interscience, 1988).

E. Administration and Use

Depending on dosage form, the pharmaceutical compositions of the preceding section may be administered in different ways, e.g., subcutaneously, intramuscularly, enterically, or the like. Preferred dosage forms are solid dosage forms which can be implanted or inserted proximate to the afflicted tissue for enhanced local delivery of drug (e.g., vaginal insertion of a suppository form), or in any selected appropriate location for the systemic delivery of drug (e.g., subcutaneous implantation of a pellet form) contained within a pellet, capsule or suppository. Parenteral delivery is preferred for administration of proteinaceous drugs such as growth factors, growth hormone, or the like.

The ortho ester polymer, upon contact with body fluids including perspiration, saliva, lymph, blood or the like (depending upon the mode of administration), undergoes gradual bioerosion with concomitant gradual exposure of the dispersed drug to the afflicted tissue. This can result in prolonged delivery (over, say, 1 to 10,000 hours, preferably 2 to 1000 hours) of effective amounts (say, 0.0001 mg/kg/hour to 10 mg/kg/hour) of the drug. The application can be repeated as necessary depending on the subject being treated, the severity of the affliction, the judgment of the prescribing physician, and the like.

EXAMPLES

The examples presented below are provided as a further guide to the practitioner of ordinary skill in the art, and are not to be construed as limiting the invention in any way.

Example 1

Under anhydrous conditions 0.3 moles of triethyl ortho propionate, 0.3 moles of 1,1,4-trihydroxymethyl cyclohexane and 20 mg of p-toluenesulfonic acid were weighed into a 500 ml round bottom flask and heated until the boiling point reached 81° C. After heating for an additional 4 hours, the solution was cooled to room temperature. Five drops of triethyl amine were added and the solvent was removed by evaporation. The residue was re-dissolved in 100 ml tetrahydrofuran and the solution was dropped into 2 l of methanol containing 1 ml of triethylamine. The precipitated polymer was collected by filtration and dried in a vacuum over. The polymer thus obtained had a M.W. of 51,000 as determined by GPC and a glass transition temperature (Tg) of 68° C.

Example 2

Following the procedure as presented in Example 1, 0.1 moles of triethyl valerate was reacted with 0.1 moles of 1,1,4-trihydroxy-methyl cyclohexane. The reaction gave a solid polymer having a Mw of 31,000 and Tg of 48.5°.

Example 3

Following the procedure described in Example 1, 0.1 moles of triethylorthoacetate was reacted with 0.1 moles of 1,1,4-trihydroxymethyl cyclohexane. The reaction yielded a polymer which precipitated out of the cyclohexane solution. The polymer was highly crystalline and was found to be insoluble in most organic solvents, such as methylene chloride, chloroform, diethylether tetrahydrofuran, ethyl acetate and acetone. It was found to be moderately soluble in dimethyl formamide and 1-methyl 2-pyrosolidinone.

Example 4

Following the procedure described in Example 1, 0.1 moles of triethylorthoacetate was reacted with 0.05 moles of 1,1,4-trihydroxymethyl cyclohexane and 0.05 moles of 1,2,6-trihydroxyhexane. The reaction yielded a polymer which was soluble in cyclohexane methylchloride, chloroform, diethylether, tetrahydrofuran and ethyl acetate. The polymer was found to have a M.W. of 22,000 as determined by GPC.

Example 5

Following the procedure described in Example 1, 0.1 moles of triethyl orthopropionate was reacted with 0.08 moles of 1,1,4-trihydorxymethyl cyclohexane and 0.02 moles of 1,2,6-trihydroxyhexane. The reaction yielded a polymer having a M.W. of 116,000 and glass transition temperature (Tg) of 56.7° C.

Example 6

This example illustrates the preparation of a bioerodible device capable of releasing drugs in sustained manner.

1.8 g of the polymer obtained by the reaction in example 5 (a polyorthopropionate) was dissolved in 5 ml of anhydrous tetrahydrofuran, and 0.2 g of 5-fluorouracil was added. Solvent was removed by evaporation. The mixture of polymer and drug was pressed into a 0.2 mm film on a curver press at 160° F. and discs of 7 mm diameter were cut and used for in vitro drug release study. The release study using pH 7.4 buffer at 37° C. showed that the discs released 5-fluorouracil linearly for a period of 7 days.

What is claimed is:

1. A method for preparing a bioerodible polymer comprising:

reacting a monomeric ortho ester having the general formula

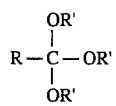

wherein R is hydrogen or alkyl of 1 to 10 carbon atoms and R' is lower alkyl with a triol having the general formula

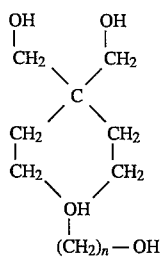

wherein n is 1 to 5 carbon atoms, to form a rigid, bioerodible ortho ester polymer containing mer units of the structure

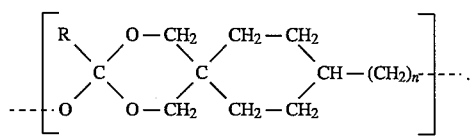

2. A compound of the formula

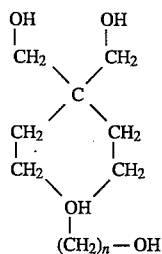

wherein n is an integer in the range of 1 to 5 inclusive.

3. A composition comprising a polymer comprising mer units of the chemical formula

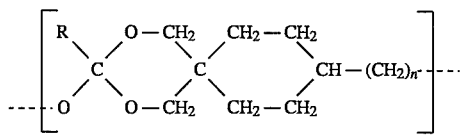

wherein R is hydrogen or $(C_1-C_{10})$alkyl, and n is 1 to 5; or co-polymers thereof or mixtures thereof.

4. The polymer of claim 3, having a molecular weight of at least about 5,000, as determined by gel permeation chromatography.

5. The polymer of claim 3, having a molecular weight of at least about 20,000, as determined by gel permeation chromatography.

6. The polymer of claim 3, having a molecular weight of at least about 50,000, as determined by gel permeation chromatography.

7. The polymer of claim 3, wherein n is 1.

8. The polymer of claim 3, wherein R is selected from the group consisting of $CH_3$, $CH_2CH_3$ and $CH_2CH_2CH_3$.

9. The polymer of claim 3, wherein R is selected from the group consisting of $CH_2CH_2CH_2CH_3$, $CH_2CH_2CH_2CH_2CH_3$ and $CH_2CH_2CH_2CH_2CH_2CH_3$.

10. The polymer of claim 3, being a copolymer.

11. A bioerodible composition, comprising the composition of claim 3; and an excipient.

12. The bioerodible composition of claim 11, wherein the excipient is selected from the group consisting of acidic and basic excipients.

13. The bioerodible composition of claim 11, further comprising an agent selected from the group consisting of colorants, diluents, odorants, carriers, excipients, stabilizers and skin permeation enhancers.

14. A solid, controlled release pharmaceutical composition comprising a therapeutic agent dispersed in the bioerodible composition of claim 11.

15. The solid, controlled release composition of claim 14, in the form of a suppository, pellet or capsule.

16. The solid, controlled release composition of claim 14, wherein the therapeutic agent is present in an amount of about 0.001 to 70wt. % of the composition.

17. The solid, controlled release composition of claim 14, wherein the therapeutic agent is selected from the group consisting of anti-infective, analgesic, antihelminthic, antiarthritic, anti-asthmatic, anti-convulsant, anti-depressant, anti-diabetic, anti-diarrheal, anti-histamine, anti-inflammatory, anti-migraine, anti-nauseant, antineoplastic, anti-parkinsonism, anti-pruritic, anti-psychotic, anti-pyretic, antispasmodic, anti-cholinergic, sympathomimetic, cardiovascular, anti-hypertensive, diuretic, and vasodilator agents, xanthine derivatives, central nervous system stimulants, cough and cold preparations, hormones, hypnotics, immunosuppressives, muscle relaxants, parasympatholytics, psychostimulants, sedatives, and tranquilizers.

18. The solid, slow release composition of claim 13, wherein the therapeutic agent is selected from the group consisting of steroid, anti-hypertensive, anti-allergic and thyroid affecting agents.

19. A controlled release method of delivering a pharmaceutical agent, comprising administering to a subject the solid pharmaceutical composition of claim 14; and allowing the composition to release, in a controlled manner, an effective amount of the pharmaceutical agent while the polymer is bioeroded and physiologically eliminated by the subject.

20. The controlled release method of claim 19, wherein the solid composition is administered subcutaneously, intramuscularly or enterically.

21. The controlled release method of claim 19, wherein the solid composition is administered locally.

22. The controlled release method of claim 21, wherein the local admininstration is conducted by implantation or insertion of the solid composition proximate to a desired target tissue.

23. A method for preparing a bioerodible polymer, comprising contacting at least one monomeric ortho ester of the chemical formula

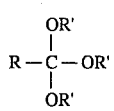

wherein R is hydrogen or $(C_1-C_{10})$alkyl, and R' is $(C_1-C_5)$alkyl, with at least one triol of the chemical formula

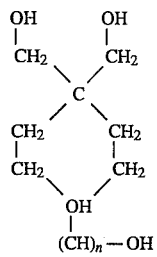

wherein n is 1 to 5, under conditions effective to form a bioerodible ortho ester polymer comprising mer units of the chemical formula

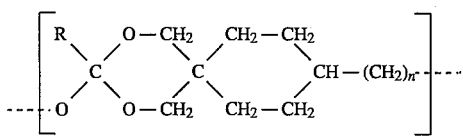

24. The method of claim 23, wherein the number of mer units in the polymer is about 2 to 1000.

25. The method of claim 24, wherein the number of mer units in the polymer is about 2 to 200.

26. The method of claim 25, wherein the number of mer units in the polymer is about 5 to 200.

27. The method of claim 23, wherein the monomeric ortho ester is reacted with more than one triol; and the bioerodible ortho ester polymer is a co-polymer.

28. A bioerodible polymer of the chemical formula

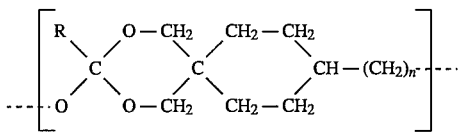

wherein R is hydrogen, and n is 1 to 5; or co-polymers thereof or mixtures thereof, prepared by the method of claim 23.

* * * * *